US00PP18715P2

(12) United States Plant Patent
Bradford

(10) Patent No.: US PP18,715 P2
(45) Date of Patent: Apr. 8, 2008

(54) NECTARINE TREE NAMED 'KAY DIAMOND VII'

(50) Latin Name: *Prunus persica*
Varietal Denomination: Kay Diamond VII

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/637,886

(22) Filed: Dec. 13, 2006

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP7,421 P 1/1991 Bradford
PP15,845 P2 7/2005 Bradford

*Primary Examiner*—Kent Bell

(57) ABSTRACT

The present invention relates to a new and distinct variety of nectarine tree, *Prunus perscia,* broadly characterized by a large size, vigorous, hardy, self-fertile, productive and regular bearing tree. The fruit matures under the ecological conditions described in the early part of June, with first picking on Jun. 6, 2006. The fruit is uniformly large in size, acidic and sweet in flavor, globose to slightly oblong in shape, clingstone in type, firm in texture, yellow in flesh color, and full red in skin color.

1 Drawing Sheet

Botanical classification: *Prunus persica.*
Variety denomination: 'KAY DIAMOND VII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'KAY DIAMOND VII'.

During the spring of 1998 I gathered fruit from several different unnamed seedlings in my experimental orchard located near Le Grand, Calif., in Merced County (San Joaquin Valley). One particular group of nectarines was early in maturing, yellow in flesh color, and clingstone in type, and was thus designated as "EN (OP)". I used embryo rescue techniques to germinate the seeds from this fruit, grew them as seedlings on their own root in my greenhouse, and upon reaching dormancy transplanted them to a cultivated area in the experimental orchard described above. During the fruit evaluation season of 2001 I selected the claimed variety as a single tree from the group of "EN (OP)", described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is most similar to 'Rose Bright' (U.S. Plant Pat. No. 15,845) nectarine by producing nectarines that are very firm in texture, clingstone in type, yellow in flesh color, and full red in skin color, but is distinguished therefrom by having leaves that are eglandular rather than having globose glands, by having a bitter instead of sweet kernel, by requiring less chilling hours during the dormant season, and by producing fruit that is larger in size and sweeter in flavor.

SUMMARY OF VARIETY

In summary, the present variety is characterized by a large size, vigorous, hardy, self-fertile, productive and regular bearing tree. The fruit matures under the ecological conditions described in the early part of June, with first picking on Jun. 6, 2006. The fruit is uniformly large in size, acidic and sweet in flavor, globose to slightly oblong in shape, clingstone in type, firm in texture, yellow in flesh color, and full red in skin color.

DRAWING

The accompanying photograph consists of four whole fruits positioned to display the characteristics of the skin color and form, one fruit divided transversely to the suture plane to reveal the flesh and stone, various leaves, an inset showing blossoms, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of shipping ripe on Jun. 8, 2006, on the original tree during its eighth growing season. All major color code designations are by reference to the Inter-Society Color Council, National Bureau of Standards. Common color names are also used occasionally.

Tree

Size: Large, reaching and maintaining a height of 11' [3.35 m.] and a spread of 10' [3.05 m.] after eight growing seasons utilizing typical dormant pruning.

Vigor: Vigorous, respond typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat Tolerance: Observed to perform adequately in typical central California climatic conditions, which typically include extended periods of heat.

Drought Tolerance: Variety is developed for commercial orchards and requires regular irrigation.

Production: Productive, thinning necessary.

Fertility: Self-fertile.

Bearing: Regular bearer with no alternate bearing yet observed.

Approximate Chilling Requirement: 500 hours.

Trunk:

*Size.*—Medium, reaching a maximum diameter of 5¾" [146 mm.] after the eighth growing season.

*Texture.*—Shaggy.

*Bark color.*—A Brownish gray [64. brGy] and Deep brown [56. deep Br] variegation.

*Lenticels.*—Approximate Number Per Square Inch: 7. Color: Moderate orange yellow [71. m.OY]. Typical Size: 3/16" [4.8 mm.] to 7/16" [11.1 mm.]. Shape: Eye-shaped to elongated.

Branches:

*Size.*—Diameter of limb is 3½" [89 mm.] measured 12" above the crotch, 2⅜" [60 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Dark orange yellow [72. d.OY] to Light olive brown [94. l.OlBr].

*Lenticels.*—Number Per Square Inch: More than 60 on second year wood. Color: Light yellowish brown [76. l.yBr]. Typical size: 1/64" [0.4 mm.] to ⅛" [3.2 mm.] on second year wood. Shape: Elongated.

Leaves:

*Size.*—Large. Average Length: 6½" [165 mm.]. Average Width: 1⅞" [48 mm.].

*Arrangement.*—Alternate.

*Thickness.*—Medium.

*Form.*—Elliptical.

*Apex.*—Acuminate.

*Base.*—Acute, with a base angle of 70 to 85 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ⅜" [9.5 mm.]. Average Thickness: 1/16" [1.6 mm.]. Color: Strong yellow green [117. s.YG].

*Stipules.*—Number: Usually 2 per leaf, up to 6 per growing tip. Average Length: 5/16" [7.9 mm.]. Color: Brilliant yellow green [116. brill.YG] becoming Deep red [13. deep R] with maturity.

*Glands.*—Eglandular.

*Leaf buds.*—Pointed, Medium.

Flower Buds:

*Hardiness.*—Hardy, with respect to central California winters.

*Diameter.*—Typically ⅜" [9.5 mm.] 1 week before bloom.

*Length.*—Typically 9/16" [14.3 mm.] 1 week before bloom.

*Form.*—Not appressed.

*Surface.*—Pubescent.

*Color.*—Moderate purplish pink [250. m.pPk].

Flowers: Perfect, complete, perigynous, usually a single pistil, typically thirty or more stamens, five sepal and petal locations alternately positioned.

*Type.*—Showy, very large.

*Average flower diameter.*—2" [50.8 mm.].

*Number of petals.*—Usually five, but 50% contain extra petal fragments with 25% being full double blossoms.

*Petal shape.*—circular to oval.

*Petal margin.*—Somewhat wavy.

*Average petal diameter.*—13/16" [20.6 mm.].

*Average petal length.*—13/16" [20.6 mm.].

*Petal apex.*—Rounded.

*Petal base.*—Rounded to somewhat truncate.

*Petal color.*—Pale pink [7. p.Pk] toward the apex, Moderate purplish red [258. mpR] toward the base.

*Anther color.*—Moderate reddish orange [37. m.rO] over a Light yellow [86. l.Y] center at bloom onset.

*Stigma color.*—Light greenish yellow [101. l.gY].

*Sepal color.*—Dark purplish red [259. d.pR].

*Sepal length.*—¼" [6.4 mm.].

*Sepal width.*—3/16" [4.8 mm.].

*Average pistil length.*—15/16" [23.8 mm.].

*Average stamen length.*—⅝" [15.9 mm.].

*Fragrance.*—Moderate.

*Blooming period.*—Early, four days before 'Rose Diamond' (U.S. Plant Pat. No. 7,421) nectarine.

*Onset of bloom.*—One percent of Feb. 15, 2006.

*Date of full bloom.*—Mar. 1, 2006.

*Duration of bloom.*—One to two weeks, dependent on ambient temperature.

*Number per cluster.*—1 to 3 with single flowers most common.

FRUIT

Maturity When Described: Shipping ripe, Jun. 8, 2006.

Date of First Picking: Jun. 6, 2006.

Date of Last Picking: Jul. 14, 2006.

Size: Uniform, large.

*Average diameter axially.*—3" [76.2 mm.].

*Average diameter across cheek plane.*—2⅞" [73.0 mm.].

*Average diameter across suture plane.*—2 15/16" [74.6 mm.].

*Typical weight.*—7.6 ounces [215 grams].

Form: Uniform, globose to slightly oblong, slightly asymmetrical.

*Longitudinal section form.*—Oval to somewhat obovate.

*Axial view.*—Round.

Suture: A sharp groove in the stem cavity, a shallow trough along the side, and a sharp groove near the apex terminating in a slight depression just beyond the pistil point.
Ventral Surface: Rounded, lipped toward the apex, slightly stronger on one side.
Lips: Unequal.
Cavity: Flaring, circular to slightly elongated in the suture plane, suture showing on one side, Very yellow [82. v.Y] stem markings typical.
*Depth.*—⅝" [15.9 mm.].
*Breadth.*—1 5/16" [13.3 mm.].
Base: Very truncate.
Apex: Rounded.
Pistil Point: Mostly apical, very short in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency,*—Astringent.
*Tendency to Crack.*—None observed.
*Color.*—Very deep red [14. v.deep R] over a Deep reddish orange [36. deep rO] background with slight Brilliant orange yellow [67. brill.OY] freckling toward the apex.
Flesh:
*Color.*—Light yellow [86. l.Y] with minimal Moderate red [15. m.R] flecking.
*Surface of pit cavity.*—Pale yellow [89. p.Y] broken fibers when twisted from stone.
*Amygdalin.*—Abundant.
*Juice.*—Abundant, rich.
*Texture.*—Very firm, crisp, melting.
*Fibers.*—Abundant, fine.
*Ripens.*—Earlier at the apex.
*Flavor.*—Acidic and sweet, typically 14 brix.
*Aroma.*—Slight.
*Eating quality.*—Very good.

STONE

Type: Clingstone.
Form: Oval.
Hilum: Narrow, oblong.
Base: Straight, rounded.
Apex: Acute, with an average tip angle of 45 degrees and a length of ⅛" [3.2 mm.].
Sides: Equal.
Surface: Irregularly furrowed toward the apex, and pitted toward the base, with a characteristic vertical furrow along each side of the ventral edge.
Ridges: Jagged.
External Color: Moderate orange yellow [71. m.OY] when freshly removed.
Pit Wall Color When Cracked: Light orange yellow [70. l.OY].
Cavity Surface Color: Light yellowish brown [76. l.yBr].
Average Pit Wall Thickness: ¼" [6.4 mm.].
Average Width: 1¼" [31.8 mm.].
Average Length: 1½" [38.1 mm.].
Average Breadth: ¾" [19.1 mm.].
Tendency To Split: Very slight.
Kernel:
*From.*—Oval.
*Skin color.*—Light yellow [86. l.Y] when first removed.
*Pellicle color.*—Light brown [57. l.Br].
*Vein color.*—Grayish yellow [90. gy.Y] when visible.
*Taste.*—Bitter.
*Viable.*—Yes, using embryo rescue.
*Average width.*—½" [12.7 mm.].
*Average length.*—¾" [19.1 mm.].
*Amygdalin.*—Abundant.

USE

Market: Fresh market and long distance shipping.
Keeping Quality: Good. Fruit quality observed to remain in good condition after 21 days in standard cold room at 36° Fahrenheit [2° Celsius].
Shipping Quality: Good.
Resistance To Insects: No unusual susceptibilities noted.
Resistance To Diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Rose Bright' (U.S. Plant Pat. No. 15,845) nectarine by producing nectarines that are very firm in texture, clingstone in type, yellow in flesh color, and full red in skin color, but is distinguished therefrom by having leaves that are eglandular rather than having globose glands, by having a bitter instead of sweet kernel, by requiring less chilling hours during the dormant season, and by producing fruit that is larger in size and sweeter in flavor.

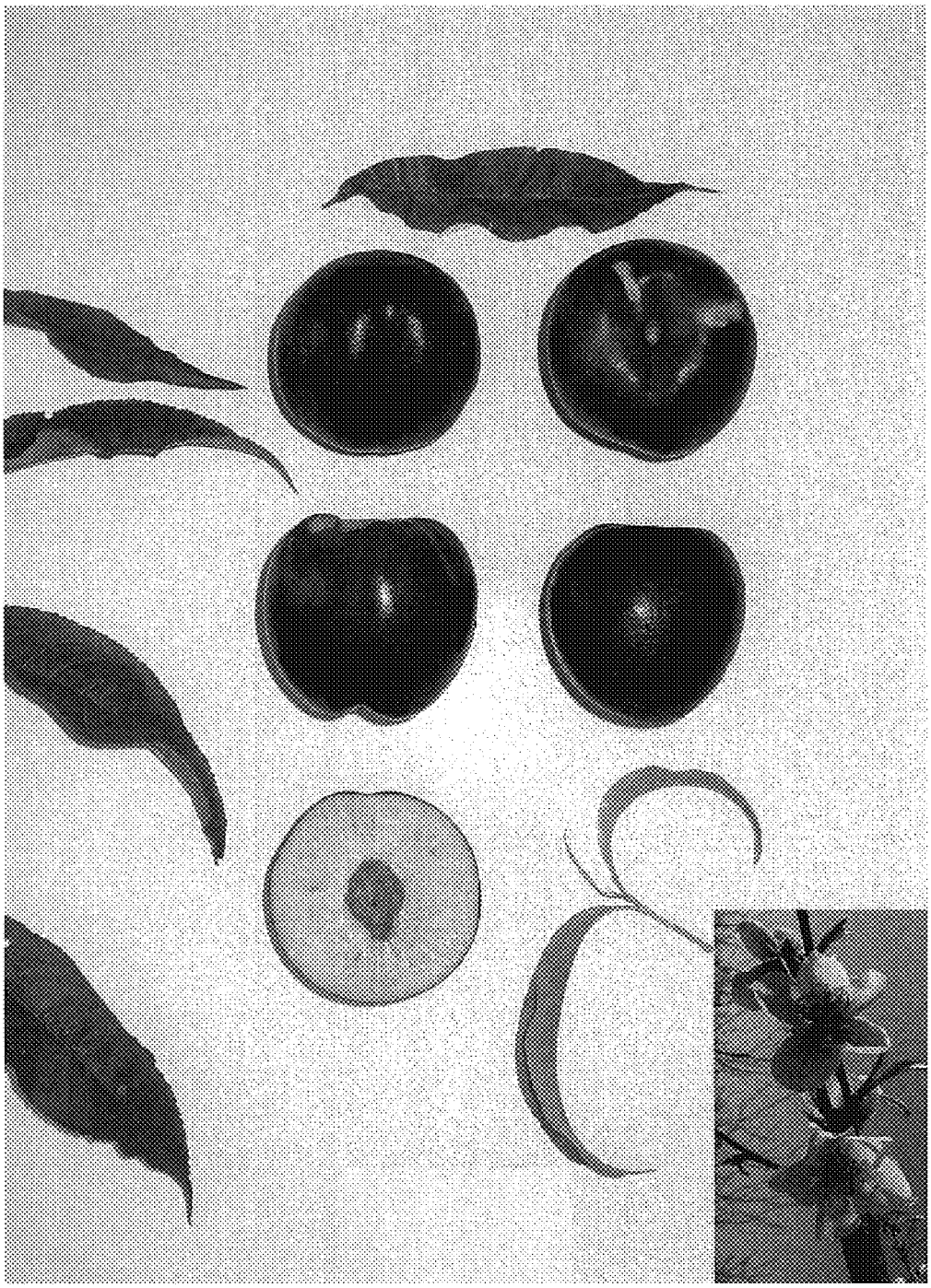

* * * * *